United States Patent [19]

Schneider

[11] Patent Number: 4,666,916
[45] Date of Patent: May 19, 1987

[54] HEXAHYDRO-(1)-BENZO-(PYRANO AND THIOPYRANO) (4,3-c)PYRIDINES, USEFUL AS SEROTIN-2 BLOCKING AGENTS

[75] Inventor: Josef A. Schneider, Millburn, N.J.

[73] Assignee: Ciba-Geigy Corporation, Ardsley, N.Y.

[21] Appl. No.: 796,348

[22] Filed: Nov. 8, 1985

[51] Int. Cl.⁴ .................. A61K 31/35; C07D 491/052; C07D 513/04
[52] U.S. Cl. .................................... 514/291; 546/80; 546/89; 546/65; 546/92
[58] Field of Search ....................... 546/80, 89, 65, 92; 514/291

[56] References Cited

U.S. PATENT DOCUMENTS

| | | | |
|---|---|---|---|
| 3,429,889 | 2/1969 | Stratgin | 546/89 |
| 3,535,327 | 10/1970 | Pars et al. | 546/89 |
| 3,576,798 | 4/1971 | Pars et al. | 546/89 |
| 3,632,595 | 1/1972 | Pars et al. | 546/89 |
| 3,787,424 | 1/1974 | Pars et al. | 546/89 |
| 3,896,137 | 7/1975 | Baile et al. | 546/89 |
| 3,915,996 | 10/1975 | Wright et al. | 546/89 |
| 3,962,448 | 6/1976 | Baile et al. | 546/89 |
| 3,991,194 | 11/1976 | Harris et al. | 546/89 |
| 4,025,630 | 5/1977 | Dren et al. | 546/89 |
| 4,042,694 | 8/1977 | Harris et al. | 546/89 |
| 4,081,449 | 3/1978 | Winn | 546/89 |
| 4,137,232 | 1/1979 | Zaugg et al. | 546/89 |
| 4,292,316 | 9/1981 | Dren et al. | 546/89 |
| 4,305,938 | 12/1981 | Zaugg | 546/89 |
| 4,604,397 | 8/1986 | Hutchison | 546/89 |

FOREIGN PATENT DOCUMENTS 751674  3/1975  South Africa ............... 546/89

OTHER PUBLICATIONS

J. Med. Chem. 19, 445 (1976), Pars et al.

Primary Examiner—Henry R. Jiles
Assistant Examiner—J. Richter
Attorney, Agent, or Firm—Norbert Gruenfeld

[57] ABSTRACT

Disclosed are the compounds of the formula

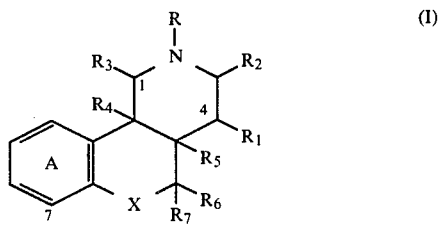

wherein X represents oxygen (O) or sulfur (S); ring A is unsubstituted or substituted by one substituent or by two or three identical or different substituents selected from hydroxy, etherified hydroxy, acyloxy, halogen, lower alkyl and trifluoromethyl; or ring A is substituted on adjacent carbon atoms by one lower alkylenedioxy; R represents hydrogen, lower alkyl, aryl-lower alkyl, lower alkenyl, lower alkynyl, aroyl-lower alkyl or aryl-lower alkyl; $R_1$ represents hydrogen, lower alkyl, lower alkylthio-lower alkyl, aryl-lower alkylthio-lower alkyl, (amino, mono- or di-lower alkylamino)-lower alkyl, acylamino-lower alkyl, (hydroxy, acyloxy or etherified hydroxy)-lower alkyl, or cyano-lower alkyl; $R_2$–$R_7$ represent hydrogen or lower alkyl; and pharmaceutically acceptable salts thereof; which are useful as serotonin-2 receptor antagonists in mammals.

15 Claims, No Drawings

＃ HEXAHYDRO-(1)-BENZO-(PYRANO AND THIOPYRANO) (4,3-c)PYRIDINES, USEFUL AS SEROTIN-2 BLOCKING AGENTS

SUMMARY OF THE INVENTION

The present invention is concerned with hexahydro-2H-[1]-benzopyrano- and benzothiopyrano[4,3-c]pyridines active as serotonin receptor antagonists and useful as therapeutic agents for the treatment of disorders responsive thereto, processes for preparing same, pharmaceutical compositions comprising said compounds, and methods of treating syndromes, conditions and diseases responsive to the effect of such a serotonin receptor antagonist by administration of said compounds or a pharmaceutical composition comprising said compounds.

DETAILED DESCRIPTION OF THE INVENTION

Particularly the invention is concerned with the novel hexahydro-2H-[1]-benzopyrano[4,3-c]pyridine and hexahydro-2H-[1]-benzothiopyrano[4,3-c]pyridine derivatives of formula I

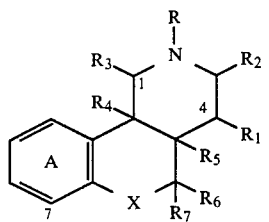

wherein X represents oxygen (O) or sulfur (S); ring A is unsubstituted or substituted by one substituent or by two or three identical or different substituents selected from hydroxy, etherified hydroxy, acyloxy, halogen, lower alkyl, aryl-lower alkyl and trifluoromethyl; or ring A is substituted on adjacent carbon atoms by one lower alkylenedioxy; R represents hydrogen, lower alkyl, lower alkenyl, lower alkynyl, aroyl-lower alkyl or aryl-lower alkyl; $R_1$ represents hydrogen, lower alkyl, lower alkylthio-lower alkyl, aryl-lower alkylthio-lower alkyl, (amino, mono- or di-lower alkylamino)-lower alkyl, acylamino-lower alkyl, (hydroxy, acyloxy or etherified hydroxy)-lower alkyl, or cyano-lower alkyl; $R_2$–$R_7$ represent hydrogen or lower alkyl; and pharmaceutically acceptable salts thereof.

Preferred are the compounds of formula I wherein $R_2$–$R_7$ represent hydrogen.

Preferred in turn are the compounds of formula I wherein X represents oxygen or sulfur; ring A is unsubstituted or substituted by one substituent or by two or three different or identical substituents selected from hydroxy, acyloxy, etherified hydroxy, aryl-lower alkyl, lower alkyl and halogen; or ring A is substituted on adjacent carbon atoms by lower alkenedioxy; R represents hydrogen or lower alkyl; $R_1$ represents hydrogen, lower alkyl, lower alkylthio-lower alkyl or lower alkoxy-lower alkyl; $R_2$–$R_7$ represent hydrogen; and pharmaceutically acceptable salts thereof.

Further preferred are the compounds of formula I wherein ring A is unsubstituted or substituted by one substituent or by two identical or different substituents selected from lower alkyl, aryl-lower alkyl, lower alkoxy, aryl-lower alkoxy and halogen; X represents oxygen or sulfur; R represents hydrogen or lower alkyl; $R_1$ represents hydrogen, lower alkyl, lower alkylthiomethyl, or lower alkoxymethyl; $R_2$–$R_7$ represent hydrogen; and pharmaceutically acceptable salts thereof.

Particularly preferred are the compounds of formula I wherein X represents oxygen or sulfur; ring A is monosubstituted or disubstituted by identical or different substituents selected from lower alkoxy of 1 to 4 carbon atoms, benzyloxy, lower alkyl of 1 to 4 carbon atoms and halogen; R represents lower alkyl of 1 to 4 carbon atoms; $R_1$ represents hydrogen, lower alkyl of 1 to 4 carbon atoms, lower $C_1$–$C_4$-alkylthio-methyl or lower $C_1$–$C_4$-alkoxymethyl; $R_2$–$R_7$ represent hydrogen; and pharmaceutically acceptable salts thereof.

A particular embodiment of the invention is represented by the compounds of formula I wherein X represents oxygen. Another particular embodiment of the invention is represented by the compounds of formula I wherein X represents sulfur.

Preferred are the compounds of formula I wherein X represents oxygen.

The compounds of formula I may be in the form of cis or trans ring-fused compounds. Depending on the nature of $R_1$ to $R_7$ and the resulting number of asymmetric carbon atoms, the compounds of formula I exist in form of a number of racemates and optical antipodes thereof.

Thus the compounds of the invention exist in the form of stereoisomers, e.g. geometric isomers, racemates, pure enantiomers or mixtures thereof, all of which are within the scope of the invention.

Preferred are the compounds of formula I with a trans 4a,10b-ring junction. The racemic products corresponding thereto are assigned the [4aS*, 10bR*] or [4aR*, 10bS*] configuration.

Particularly preferred are the compounds of the formula II

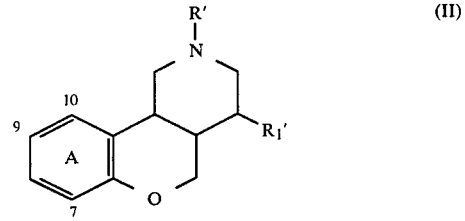

preferably with a trans 4a,10b-ring junction, wherein ring A is disubstituted, preferably at the 9 or 10 position by lower alkoxy of 1 to 4 carbon atoms, and, preferably at the 7-position by lower alkyl of 1 to 4 carbon atoms or halogen; R' represents lower alkyl of 1 to 4 carbon atoms; $R_1'$ represents hydrogen or lower $C_1$–$C_4$-alkylthiomethyl; and pharmaceutically acceptable salts thereof.

Most preferred are the compounds of formula II with a trans-4a,10b-ring junction wherein ring A is substituted at the 7-position by lower alkyl of 1 to 3 carbon atoms, bromo or chloro, and substituted at the 9-position by lower alkoxy of 1 to 3 carbon atoms; R' represents lower alkyl of 1 to 3 carbon atoms; $R_1'$ represents hydrogen or $C_1$–$C_3$-alkylthiomethyl; and pharmaceutically acceptable salts thereof.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group is straight chain or branched and preferably contains 1 to 4 carbon atoms, and represents for example ethyl, propyl, butyl, and advantageously methyl.

A lower alkoxy group is straight chain or branched and preferably contains 1 to 4 carbon atoms, and represents for example methoxy, ethoxy, propoxy.

A lower alkenyl group preferably contains 3 or 4 carbon atoms and represents for example allyl or crotyl.

A lower alkynyl group preferably contains 3 or 4 carbon atoms and represents for example propargyl.

A lower alkylthio group is straight chain or branched and represents, for example, methylthio, ethylthio, propylthio, butylthio.

Lower alkanoyl is preferably acetyl, propionyl or butyryl.

Aroyl is preferably benzoyl or benzoyl substituted by one to three of lower alkyl, lower alkoxy, halogen or trifluoromethyl.

Heteroaroyl is preferably thienoyl, pyrrolyl, 2-, 3- or 4-pyridylcarbonyl, advantageously nicotinoyl.

Aryl, as in aryl-lower alkyl, is preferably phenyl, 1- or 2-naphthyl, or phenyl substituted by one to three of lower alkyl, lower alkoxy, halogen or trifluoromethyl; and aryl-lower alkyl is advantageously benzyl or phenethyl optionally substituted on the benzene ring by one to three of lower alkyl, lower alkoxy, halogen or trifluoromethyl; or aryl lower alkyl is advantageously 1- or 2-naphthylmethyl or 1- or 2-naphthylethyl.

Lower alkanoyloxy is preferably acetoxy or propionyloxy; lower alkanoylamino is preferably acetamido or propionamido.

Aroyloxy is preferably benzoyloxy or benzoyloxy substituted on the benzene ring by one to three of lower alkyl, lower alkoxy, halogen or trifluoromethyl, or heteroaroyloxy.

Heteroaroyloxy is preferably 2-, 3- or 4-pyridylcarbonyloxy, advantageously nicotinoyloxy.

Halogen is preferably bromo, but may also be fluoro, chloro or iodo.

Lower alkylenedioxy represents preferably ethylenedioxy or methylenedioxy.

Etherified hydroxy represents preferably lower alkoxy, e.g. methoxy or ethoxy; lower alkenyloxy, e.g. allyloxy; lower alkynyloxy, e.g. propargyloxy; $C_{3-6}$-cycloalkyl-lower alkoxy, e.g. cyclopropylmethoxy; aryl-lower alkoxy, e.g. benzyloxy unsubstituted or substituted on the phenyl ring e.g. the lower alkyl, halogen or lower alkoxy, such as methyl, chloro or methoxy respectively; pyridyl-($C_1$-$C_4$)-alkoxy, e.g. pyridylmethoxy; naphthyl-lower alkoxy, e.g. 1- or 2-naphthyl-(methoxy or ethoxy); also fluorenyloxy, e.g. 9-fluorenyloxy; fluorenyl-lower alkoxy, e.g. 1-fluoroenyl-(methoxy or ethoxy).

Etherified hydroxy may also represent the grouping A

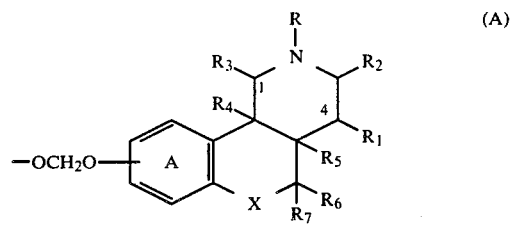

wherein ring A may be further substituted, preferably by halogen, lower alkyl or trifluoromethyl; R, $R_1$–$R_7$ and X have meaning as defined for compounds of formula I, and preferably wherein the —$OCH_2O$— linking moiety is attached at the 9-position of the tricyclic ring system. The resulting compounds of formula I substituted by said etherified hydroxy groups are advantageously the symmetrical bis compounds represented by the formula Ia

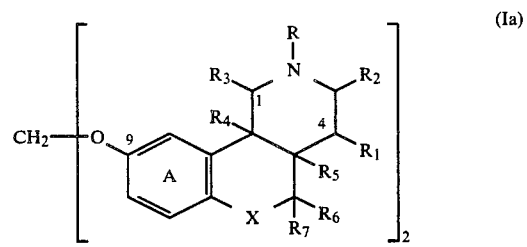

wherein ring A, R, $R_1$–$R_7$ and X have meaning as defined above for grouping A.

Lower alkylthio-lower alkyl is preferably straight chain $C_1$–$C_4$-alkylthio-$C_1$–$C_4$-alkyl, advantageously $C_1$–$C_4$-alkylthiomethyl.

Aryl-lower alkylthio-lower alkyl is preferably aryl-$C_1$–$C_4$-alkylthio-$C_1$–$C_4$-alkyl, advantageously aryl-$C_1$–$C_4$-alkylthiomethyl, wherein aryl has meaning as defined above.

(Amino, mono- and di-lower alkylamino)-lower alkyl represent preferably (amino, mono- and di-$C_1$–$C_4$-alkylamino)-methyl.

(Hydroxy, acyloxy, etherified hydroxy)-lower alkyl represent preferably (hydroxy, $C_1$–$C_4$-alkanoyloxy or $C_1$–$C_4$-alkoxy)-methyl.

Cyano-lower alkyl represents preferably cyanomethyl.

Acylamino represents preferably lower alkanoylamino, aryl-lower alkanoylamino, aroylamino, heteroaroylamino, lower alkoxycarbonylamino, and benzyloxycarbonylamino wherein the respective groups have the meaning as defined above. Acylamino also represents phthalimido.

Acyloxy represents preferably lower alkanoyloxy, aroyloxy, heteroaroyloxy wherein the respective groups have the meaning as defined above.

Mono- or di-lower alkylamino is preferably mono- or di-(methyl, ethyl, propyl)-amino.

Pharmaceutically acceptable salts are acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycolic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The novel compounds of the invention are active in state of the art in vitro and in vivo test systems indicative of serotonin-2 receptor antagonism for the treatment of certain central nervous system, cardiovascular and gastrointestinal disorders in mammals.

Excessive serotonin-2 receptor activity is implicated in central nervous system disorders such as anxiety, depression and mania; in cardiovascular disorders, such as hypertension; and in gastrointestinal disorders such as ulcers.

The above-cited properties are demonstrable in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-5}$ molar and $10^{-9}$ molar concentrations. The dosage in vivo may range between about 0.10 and 50 mg/kg/day, preferably between about 0.50 and 25 mg/kg/day, advantageously between about 1.0 and 10 mg/kg/day.

The serotonin-2 (HT-2) receptor binding properties, indicative of the serotonin-2 antagonist activity of the compounds of the invention, are determined in vitro by determining their ability to inhibit the specific binding of $^3$H-ketanserin, essentially as described by Battaglia et al in Life Sciences 33, 2011 (1983), in membrane preparations of frontal/parietal cortex from male Sprague-Dawley rats (200-225 g). $IC_{50}$ values, representing the concentration of compound required to displace 50% of specific binding of 0.4 nM of $^3$H-ketanserin, are determined by log-logit analysis of the specific binding data. Selectivity for the HT-2 receptors can be determined by also measuring specific binding to serotonin-1 (HT-1) receptors, e.g. according to Middlemiss, D. N. and Fozard, J. R. in Eur. J. Pharmacol. 90, 151 (1980).

The serotonin-2 antagonism or blockade is determined in vivo by measuring the inhibition of the head twitch induced by 5-hydroxytryptophane (the metabolic precursor of serotonin) in the rat. The head twitch test for assessing central nervous system serotonin-2 receptor antagonism in the rat is described in Neuropharmacology 16, 663 (1977) and in J. Pharmacol. Exp. Ther. 228, 133 (1984). The test is carried out as follows:

Male Wistar rats (120-180 g) are fasted for 18 hr prior to testing but allowed water ad libitum. All animals are pretreated with the peripheral decarboxylase inhibitor alpha-methyl-DOPA hydrazine (carbidopa 25 mg/kg i.p., 4.0 ml/kg) followed 30 min later by 5-hydroxytryptophan (5HTP 100 mg/kg s.c., 4.0 ml/kg). Ninety minutes after receiving 5HTP, the rats are placed individually in plexiglas observation cages and the frequency of head twitches for each animal is counted over a 10 min observation period. The test compound or vehicle is administered at either 0.5 hr at 1.0 ml/kg i.p. or at 1, 2 or 4 hr at 10 ml/kg p.o. prior to the observation period. $ED_{50}$ values are determined by probit analysis.

The compounds of the invention are effective in the serotonin-2 receptor binding assay at concentrations as low as about 15 nM. They are also effective in the head twitch test at doses as low as about 1 mg/kg in the rat.

Illustrative of the invention, the compound [4R*,4aS*,10bR*]-7-bromo-4-(ethylthiomethyl)-1,3,4,4a,5,10b-hexahydro-9-methoxy-2-methyl-2H-[1]benzopyrano[4,3-c]-pyridine hydrochloride has an $IC_{50}$ of 22 nM ($2.2 \times 10^{-8}$M) in the serotonin-2 receptor assay (involving the specific binding of $^3$H-ketanserin) and an $ED_{50}$ of 1.1 mg/Kg ip (at 30 minutes) and 0.71 mg/Kg po (at 1 hour) in the head twitch test.

Further biological effects of the compounds of the invention attributable to the serotonin-2 blocking properties of the compounds, e.g. effects on the central nervous and cardiovascular systems, can be demonstrated using animal tests well-known in the art. For example, anxiolytic properties are demonstrated in the standard Cook-Davidson conflict model in the rat; an increase in punished operant performances is indicative of an antianxiety effect. Antihypertensive properties are demonstrated in the spontaneous hypertensive rat.

The aforesaid advantageous properties render the compounds of the invention useful in mammals, especially as serotonin-2 receptor antagonists, for the treatment of psychotropic disorders such as anxiety, depression and mania, for the treatment of gastrointestinal disorders such as ulcers, and for the treatment of cardiovascular disorders such as hypertension.

The compounds of the invention (represented by formulae I and II) can be prepared using the following processes:

(a) reducing a compound of the formula

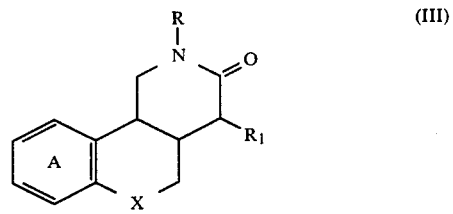

(III)

which additionally may contain groups $R_3$–$R_7$ as designated in formula I and wherein ring A, X, R, $R_1$, $R_3$–$R_7$ have meaning as defined hereinabove;

(b) reducing a compound of the formula identical to formula I, except for the presence of a carbon to carbon double bond within the two heterocyclic rings or the presence of a carbon to nitrogen double bond (imine or iminium bond);

(c) cyclizing a compound of the formula IV or IVa

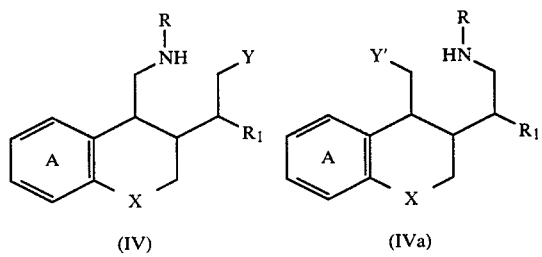

(IV)          (IVa)

which additionally may contain groups $R_2$–$R_7$ as designated in formula I and wherein ring A, X, R, $R_1$–$R_7$ have meaning as defined hereinabove, Y and Y' represent esterified hydroxy;

(d) reducing a compound of formula V

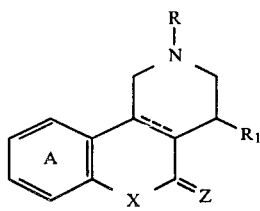
(V)

which additionally may contain groups $R_2$ to $R_5$ as designated in formula I, wherein the dotted line represents the position of an optional double bond, Z represents oxo and ring A, X, R and $R_1$-$R_5$ have meaning as previously defined hereinabove;

(e) to obtain a compound of formula I wherein $R_6$ and $R_7$ are identical and represent lower alkyl, condensing a compound of formula V above with a lower alkyl organometallic reagent, and, if required, reducing the ring junction carbon to carbon double bond;

(f) saturating the pyridine (or pyridinium, if R is different from hydrogen) ring in a compound of the formula

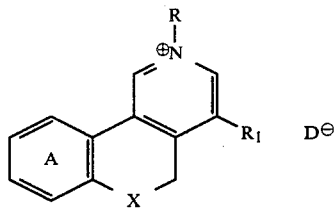
(VI)

which additionally may contain groups $R_2$, $R_3$, $R_6$ and $R_7$ as designated in formula I and wherein ring A, X, R, $R_1$-$R_3$, $R_6$, $R_7$ have meaning as defined hereinabove, and $D^\ominus$ represents the anion of an organic or inorganic acid;

(g) cyclizing a compound of the formula

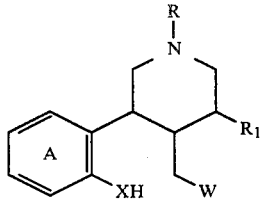
(VII)

which additionally may contain groups $R_2$-$R_7$ as designated in formula I and wherein ring A, X, R and $R_1$-$R_7$ have meaning as previously defined hereinabove; W represents esterified hydroxy;

(h) cyclizing a compound of the formula

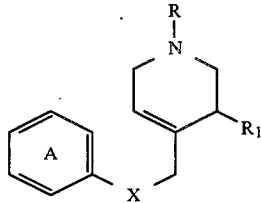
(VIII)

which additionally may contain groups $R_2$-$R_4$, $R_6$ and $R_7$ as designated in formula I and wherein ring A, X, R, $R_1$-$R_4$, $R_6$ and $R_7$ have meaning as defined hereinabove;

(i) reducing a compound of the formula

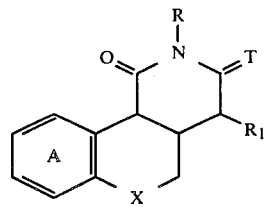
(IX)

which additionally may contain groups $R_4$-$R_7$ as designated in formula I and wherein ring A, X, R, $R_1$, $R_2$ and $R_4$-$R_7$ have meaning as defined hereinabove, and T represents oxo or one hydrogen together with $R_2$;

(j) for a compound of formula I wherein R represents lower alkyl or aryl-lowr alkyl, reducing a compound of the formula

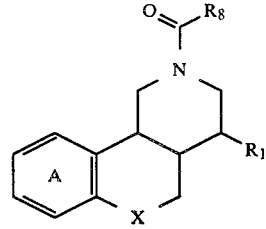
(X)

which additionally may contain groups $R_2$-$R_7$ as designated in formula I and wherein ring A, X, $R_1$-$R_7$ have meaning as defined hereinabove; $R_8$ represents hydrogen or aryl; or $R_8$ represents lower alkyl or aryl-lower alkyl with one carbon atom less in the lower alkyl portion than the corresponding lower alkyl or aryl-lower alkyl represented by R in formula I;

(k) cyclizing a compound of the formula

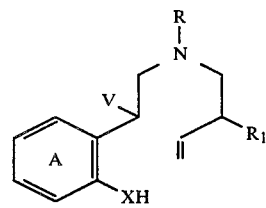
(XI)

which additionally may ontain the groups $R_2$-$R_7$ as designated in formula I, and wherein ring A, X, R, $R_1$-$R_7$ have meaning as defined hereinabove, and V represents esterified hydroxy; or (l) derivatizing a compound of the formula

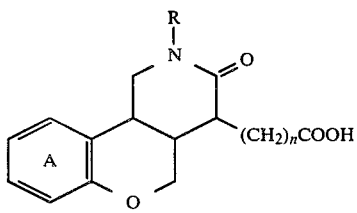
(XII)

or a reactive functional derivative thereof, e.g. a lower alkyl ester, which may additionally contain groups $R_3$ to $R_7$ as designated in formula I and wherein n is 0 or 1 to 6, ring A, X, R, $R_3$ to $R_7$ have meaning as defined hereinabove, by decarboxylation and reduction, or by reduction and side chain transformation; and carrying out all the said processes while, if necessary, temporarily protecting any interfering reactive group(s) in all these processes, and then isolating the resulting compound of the formula I; and, if desired, converting a resulting compound of formula I into another compound of the invention, and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

A reactive esterified hydroxy group in any of the herein mentioned processes is hydroxy esterified by a strong acid, especially a strong inorganic acid, such as a hydrohalic acid, especially hydrochloric, hydrobromic or hydriodic acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example phenylsulfonyloxy, 4-methylphenylsulfonyloxy (tosyloxy) or methylsulfonyloxy.

A reactive functional derivative of a carboxylic acid within the context of the reactions mentioned herein represents e.g. an acyl halide such as the acid chloride, the anhydride of said acid, a mixed anhydride e.g. such derived from a lower alkyl halocarbonate such as ethyl chloroformate, a reactive ester, e.g. a lower alkyl ester such as an ethyl or methyl ester or an optionally substituted phenyl ester, or an amide, e.g. such derived from imidazole (prepared from N,N-carbonyldiimidazole).

In starting compounds and intermediates therefor which are converted to the compounds of the invention in a manner described herein, functional groups present, such as carbonyl (formyl or keto), carboxy, amino, hydroxy and sulfhydryl groups, are optionally protected by conventional protecting groups that are common in preparative organic chemistry. Protected carbonyl, carboxy, amino, hydroxy and sulfhydryl groups are those that can be converted under mild conditions into free carbonyl, carboxy, amino, hydroxy and sulfhydryl groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carbonyl group, carboxy group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York 1965, as well as in Houben-Weyl, "Methoden der Organischen Chemie", Vol. 15/1, George Thieme Verlag, Stuttgart, 1974.

The preparation of the compounds of the invention according to process (a) is preferably carried out by reduction with a simple or complex hydride reducing agent known in the art for reduction of an amide function e.g. lithium aluminum hydride or diborane in an inert solvent such as tetrahydrofuran or diethyl ether, advantageously at room or elevated temperature.

The preparation of compounds of the invention according to process (b) is carried out according to methods well-known in the art for the reduction of double bonds, such as diimide, or particularly for the compounds of formula I wherein X represents oxygen, with hydrogen under hydrogenation conditions, preferably in the presence of a catalyst such as palladium on charcoal, or with lithium in liquid ammonia, or when the compound to be reduced represents an enamine, an imine or iminium salt with a chemical reducing agent such as sodium cyanoborohydride under conditions well-known in the art, at room or elevated temperature in a polar solvent such as isopropanol.

The process according to process (c) is carried out with or without basic catalysts such as triethylamine, sodium or potassium carbonate in an inert solvent, as is well-known in the art for N-alkylation reactions.

The preparation of compounds of the invention according to process (d) is carried out preferably by reduction with a simple or complex metal hydride reducing agent, advantageously in the presence of a Lewis acid, e.g. with lithium aluminum hydride or sodium borohydride in the presence of boron trifluoride or aluminum chloride. The optional reduction of the double bond is carried out as described under process (b).

The preparation of compounds of the invention according to process (e) is carried out preferably by condensation with an excess of a lower alkyl magnesium halide (a Grignard reagent) in a solvent such as a mixture of diethyl ether and anisole at a temperature ranging preferably from room temperature to a boiling point of the solvent. The optional saturation of the double bond is carried out as described under process (b).

The process according to process (f) is carried out according to methods well-known in the art for the reduction of pyridine and pyridinium compounds, e.g. advantageously for the compounds wherein X=O by catalytic hydrogenation to the compounds of formula I, or by reduction with simple or complex metal hydrides, such as sodium borohydride or aluminum hydride to the compounds having formula I except for a 4a,10b-double bond, followed by the reduction of the double bond as described under process (b).

The preparation of compounds of the invention according to process (g) is carried out in a conventional manner, usually in the presence of a solvent or mixture of solvents, and, if necessary, whilst cooling or heating, for example at a temperature range of from approximately $-20°$ C. to approximately $150°$ C., and/or in an inert gas atmosphere, for example a nitrogen atmosphere. The reaction is carried out advantageously in the presence of a base, such as an inorganic base, for example an alkali metal or alkaline earth metal carbonate, hydride or hydroxide, or in the presence of an organic base, such as an alkali metal lower alkoxide, or a tertiary amine such as triethylamine or pyridine.

Cyclization process (h) is preferably carried out in the presence of a protic acid such as polyphosphoric acid or a Lewis acid such as boron trifluoride or aluminum chloride under conditions well-known in the art for Friedel-Crafts alkylation reactions with or without a suitable organic anhydrous solvent.

The preparation according to process (i) is carried out as described under process (a) above.

The preparation according to process (j) is likewise carried out as described under process (a) above.

The cyclization according to process (k) is carried out essentially as described for process (g).

Derivatization according to process (l) is carried out according to methods well-known in the art and as exemplified herein.

Decarboxylation of a compound of formula XII, particularly wherein n=0 to a compound of formula III wherein $R_1$ represents hydrogen is carried out preferably by heating at an elevated temperature, optionally in a high boiling inert solvent such as ethylene glycol or xylene, advantageously at a temperature ranging between 150° C. and 250° C. Subsequent reduction to a compound of formula I wherein $R_1$ represents hydrogen is carried out as described for process (a).

A corresponding ester of formula XII is converted to the free carboxylic acid according to methods well-known in the art, advantageously with an aqueous solution of an alkali metal hydroxide or an alkali metal cyanide.

The compounds of formula XII or esters, e.g. lower alkyl esters, can be reduced, e.g. with diborane to compounds of formula I wherein $R_1$ represents hydroxy-lower alkyl. Said compounds can be further transformed into other compounds of formula I using methodology well-known in the art, as illustrated herein.

Said compounds of the formula I, e.g. wherein $R_1$ is hydroxymethyl, are first converted to a reactive esterified derivative thereof, e.g. by condensation with a lower alkylsulfonyl halide to obtain compounds wherein $R_1$ represents e.g. lower alkylsulfonyloxymethyl which can be further derivatized as follows:

(a') condensation with e.g. a lower alkanol, a lower alkylmercaptan, an aryl-lower alkyl mercaptan, ammonia, a mono- or di-lower alkylamine, preferably in the presence of a base leads to the compounds of formula I wherein $R_1$ represents lower alkoxymethyl, lower alkylthiomethyl, aryl-lower alkylthiomethyl, aminomethyl, mono- or di-lower alkylaminomethyl, respectively.

(b') reduction, e.g. with lithium triethylborohydride, leads to compounds of formula I wherein $R_1$ is methyl.

(c') condensation with an alkali metal cyanide, e.g. potassium cyanide, leads to the compounds of formula I wherein $R_1$ is cyanomethyl. Such may in turn be converted to the carboxylic acids of formula XII wherein n is 1. Further derivatization as described for the carboxylic acids of formula XII wherein n is 0 leads to the corresponding compounds of formula I, e.g. wherein $R_1$ represents e.g. lower alkoxyethyl, lower alkylthioethyl, aryl-lower alkylthioethyl, aminoethyl, mono- or di-lower alkylaminoethyl.

(d') condensing with a di-lower alkyl malonate, such as diethyl malonate in the presence of base, such as sodium ethoxide, hydrolyzing the resulting malonate ester, decarboxylating the resulting malonic acid to obtain a carboxylic acid of formula XII wherein n represents the integer 2. Further derivatization, as described for the compounds of formula XII wherein n is zero, leads to corresponding compounds of formula I wherein $R_1$ represents e.g. lower alkoxypropyl, lower alkylthiopropyl, aryl-lower alkylthiopropyl, (amino, mono- or di-lower alkylamino)propyl.

The compounds of formula I or intermediates leading thereto can be converted into other compounds of formula I or corresponding intermediates, using chemical methodology known in the art and as illustrated herein.

Compounds of formula I, Ia or II wherein the nitrogen substituent R or R' represents hydrogen may be converted to the compounds wherein R and R' represents lower alkyl, lower alkenyl, lower alkynyl, aroyl-lower alkyl or aryl-lower alkyl e.g. by (a) reaction with a reactive esterified derivative e.g. a halide, of a corresponding lower alkanol, lower alkenol, lower alkynol, aroyl-lower alkanol or aryl-lower alkanol; (b) reaction with the corresponding lower alkylcarboxaldehyde, aryl-lower alkylcarboxaldehyde or arylcarboxaldehyde to yield a compound wherein R or R' represents lower alkyl or aryl-lower alkyl in the presence of a reducing agent such as sodium cyanoborohydride; or (c) reductive alkylation with formaldehyde and formic acid to yield the compound wherein R or R' represents methyl.

Compounds wherein R or R' is methyl can also be prepared by reacting the corresponding compounds wherein R or R' represents hydrogen with a lower alkyl- or phenyl lower alkyl-haloformate, such as ethyl chloroformate, to obtain compounds wherein R or R' is alkoxycarbonyl or phenylalkoxycarbonyl, and reducing said acyl derivatives with simple or complex light metal hydrides such as lithium aliminum hydride, sodium tri-t-butoxy- or bis-(2-methoxyethoxy)-aluminum hydride.

The compounds substituted on ring A by hydroxy (phenols) may be converted to the compounds substituted by etherified hydroxy as defined above using methods known in the art for the alkylation of phenols, such as reacting a phenol of formula I in the presence of a base, optionally under conditions of phase transfer catalysis with a reactive esterified derivative of the etherifying alcohol, e.g. a halo derivative thereof, or reacting a phenol of formula I with the alcohol corresponding to the etherifying group in the presence of a condensing reagent such as dicyclohexylcarbodiimide.

The compounds of formula I substituted on ring A by hydroxy (phenols) may be converted to the compounds of formula I wherein etherified hydroxy represents the grouping A by reacting a phenol of formula I with bis(esterified hydroxy)-substituted methane, preferably diiodomethane, in the presence of a base and advantageously under conditions of phase transfer catalysis.

Halogen, particularly bromo or chloro, may be introduced in ring A by treatment with chlorine or bromine in a polar solvent such as acetic acid, as illustrated in the examples.

Compounds wherein ring A is substituted e.g. by acyloxy, such as lower alkanoyloxy or aroyloxy, may be converted to compounds of formula I wherein ring A is substituted by hydroxy using hydrolysis with e.g. aqueous acid, such as hydrochloric acid, or with aqueous alkali, such as lithium or sodium hydroxide.

Conversely, the conversion of compounds wherein ring A is substituted by hydroxy to compounds of formula I wherein ring A is substituted by acyloxy, such as alkanoyloxy or aroyloxy may be carried out by condensation with a corresponding carboxylic acid, or reactive derivative thereof, according to acylation (esterification) procedures well-known to the art.

The conversion of the compounds wherein ring A is substituted by etherified hydroxy, e.g. lower alkoxy, to the compounds wherein ring A is substituted by hydroxy is carried out by methods well-known in the art, e.g., with a mineral acid, such as hydriodic acid, or, advantageously for compounds wherein etherified hydroxy is methoxy, with e.g. boron tribromide in methylene chloride, with sodium or lithium diphenylphosphide in tetrahydrofuran, or by heating with pyridine hydrochloride.

The conversion of compounds wherein ring A is substituted e.g. by optionally substituted benzyloxy to compounds wherein ring A is substituted by hydroxy is advantageously carried out by hydrogenolysis using hydrogen in the presence of a catalyst e.g. palladium.

Compounds wherein the nitrogen substituent R or R' represents benzyl or optionally substituted benzyl, may be hydrogenolyzed to the corresponding compounds wherein R or R' represent hydrogen, for example with hydrogen in the presence of a hydrogenolysis catalyst, e.g. palladium on charcoal.

Unsaturated compounds, such as those bearing an alkenyl or alkynyl radical, may also be hydrogenated with catalytically activated hydrogen to obtain compounds of formula I or intermediates bearing the corresponding alkyl radical.

Compounds halo substituted (particularly by bromo) on ring A may be converted to compounds wherein bromo on ring A is replaced by e.g. lower alkyl, by treatment first with a strong base such as butyl lithium and subsequently with a reactive electrophile such as a lower alkyl halide.

The starting materials of formula III and of formula XII are advantageously prepared by cyclization of the compounds of formula XIII

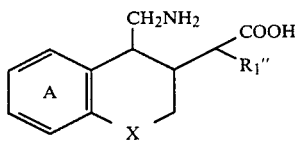

XIII or a reactive carboxyclic acid functional derivative thereof which additionally may contain groups R and $R_3$-$R_7$ as defined hereinabove, and wherein ring A, X, R and $R_3$ to $R_7$ have meaning as defined hereinabove, and $R_1''$ represents either $R_1$ or $R_1'$ as defined in formula I or II, or represents $(CH_2)_n$ COOH as defined in formula XII, under conditions well-known in the art for the formation of an amide bond.

The compounds of formula XIII can be prepared in situ by reduction of corresponding nitriles of formula XIV

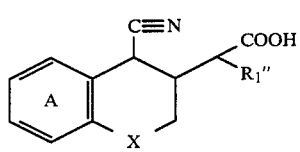

XIV wherein ring A, X, $R_1''$ and $R_3$-$R_7$ have meaning as defined above.

More specifically, optionally substituted chroman-4-ones or thiochroman-4-ones are condensed e.g. with trimethylsilyl cyanide to give the corresponding 4-cyano-2H-[1]-benzo-pyrans or 4-cyano-2H-[1]thiobenzopyrans. Subsequent condensation thereof with a di-lower alkyl ester of malonic acid yields compounds of formula XIV wherein $R_1''$ represents carboxy as a di-lower alkyl ester thereof. Reduction thereof can be carried out e.g. with sodium borohydride/cobalt chloride or under conditions of catalytic hydrogenation, for example with platinum in glacial acetic acid, to yield compounds of formula XIII which are cyclized, advantageously in situ, to yield lower alkyl esters of the compounds of formula XII wherein R is hydrogen and n is 0, which can be separated into the cis and trans isomers and derivatized as described under process (1).

The starting materials of formula XIV wherein $R_1''$ represents carboxy wherein the substituents on the heterocyclic ring are trans can in turn be prepared directly by the following illustrative procedure.

Optionally substituted 2H-[1]-benzopyrans or 2H-[1]-benzothiopyrans are reacted with e.g. dimethyl diazomalonate in the presence of cuprous iodidetrimethylphosphite complex to yield the cis cyclopropyl fused compounds, namely the dimethyl esters of the corresponding cis-1,1a,2,7b-tetrahydrobenzo[b]cyclopropa[d]pyran-1,1-dicarboxylic acids. Subsequent opening of the cyclopropane ring, advantageously with diethyl aluminum cyanide yields the trans isomers of the dimethyl ester of compounds of formula XIV wherein $R_1''$ represents carboxy.

The starting materials of formula IV or IVa may be prepared, advantageously in situ, from esters of 4-carboxy-2H-[1]benzopyrans or 4-carboxy-2H-[1]benzothiopyrans by Michael condensation with the appropriately alpha-($R_1$-substituted) malonic acid ester, monodecarboxylating the resulting malonic acid or ester, reducing the resulting dicarboxylic acid or ester to the corresponding diol, converting to a reactive derivative, e.g. the dimesylate and condensing with an amine of the formula $RNH_2$ wherein R has meaning as defined hereinabove. The starting materials of formula IX wherein T represents oxo are in turn prepared by condensation of the above-obtained intermediate dicarboxylic acid or ester with an amine $RNH_2$.

The starting materials of formula V may be prepared e.g. according to the general methodology illustrated in U.S. Pat. No. 3,535,327 and optionally hydrogenating the ring junction double bond.

Alternately starting materials of formula V lacking the ring junction double bond may be prepared by condensing an appropriately substituted 4-carboxy-1,2,5,6-tetrahydropyridine derivative with an appropriately o-hydroxy substituted phenyl organometallic reagent, e.g. a copper lithium organometallic reagent, to obtain an appropriately substituted 3-(o-hydroxyphenyl)-4-carboxypiperidine derivative which is cyclized to the lactone of formula V.

Starting materials of formula VII may be obtained by reduction of the carboxy or functionalized carboxy function in the appropriately substituted 3-(o-hydroxyphenyl)-4-carboxypiperidines described above to the corresponding alcohols which may then be converted to reactive esterified derivatives thereof.

The starting materials of formula VI wherein R=H may be obtained by condensing e.g. appropriately substituted 4-chloromethylpyridine derivatives with appropriately substituted phenols to the appropriately substituted 4-(phenoxymethyl)pyridine derivatives which are then reacted with a Lewis acid. The quaternary salts are obtained by subsequent N-alkylation.

The starting materials for process (b), wherein a double bond is at the ring junction, may be obtained by reducing starting materials of formula VI with e.g. a borohydride reducing agent.

The starting materials of formula VIII may be prepared by selectively reducing e.g. with a borohydride reducing agent, the above-cited appropriately substituted 4-(phenoxymethyl)-pyridine or pyridinium derivatives.

The starting materials of formula IX may be prepared by Michael condensation of e.g. a lower alkyl ester of 4-carboxy-2H-[1]benzopyran or 4-carboxy-2H-[1]benzothiopyran with an appropriately alpha-($R_1$-substituted)cyanoacetic acid ester, hydrolyzing and monodecarboxylating the resulting diester, reducing the cyano group, cyclizing the resulting amino acid or ester to a compound of formula IX wherein R represents hydrogen, and if required, N-alkylating to compounds of formula IX.

The starting materials of formula X may be prepared by N-acylating a compounds of formula I wherein R represents hydrogen with a caboxylic acid of formula $R_8$-COOH, wherein $R_8$ has meaning as defined for compounds of formula X, or a reactive functional derivative thereof.

The starting materials of formula XI may be prepared by converting appropriately alpha-substituted 3-butenoic acid amides to the corresponding 3-butenylamines, condensing said butenylamines with e.g. appropriately substituted o-hydroxyphenyloxiranes to compounds of formula XI wherein X represent O and V represents hydroxy. Conversion to compounds of formula XI wherein V represents reactive esterified hydroxy, e.g. halo, may be carried out by conventional methods.

The 2H-[1]benzopyran, 2H-[1]benzothiopyran, chroman-4-one and thiochroman-4-one starting compounds are prepared according to known methods or as illustrated herein.

With reference to the above reactions and as mentioned above, it may be advantageous to appropriately protect the potentially reactive, e.g. amino, carboxy, hydroxy, or other interfering substituents in accordance with protective techniques well-known to the art, e.g. as illustrated below, so that interfering reactions are avoided, by protecting such substituents prior to the desired reaction and subsequently, if necessary removing the protective groups to obtain the desired compounds, e.g. of formula I, or intermediates.

For instance, a basic primary or secondary amine may be protected in the form of easily cleaved amides, e.g. as acyl derivatives such as the benzyloxycarbonyl (carbobenzyloxy) or the t-butyloxycarbonyl derivatives, or any other easily removable N-protecting groups.

A carboxy group may be protected in the form of an easily cleaved ester, e.g. the benzyl ester, the t-butyl ester, and the like as commonly used.

A hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

In a resulting protected compound of formula I or intermediate, in which one or more of the functional groups are protected, the protected functional groups can be liberated, in a manner, known per se, e.g. by means of solvolysis, e.g. hydrolysis with acid, or by means of reduction, e.g. hydrogenolysis.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Whenever desirable, the above processes are carried out after first suitably protecting any potentially interfering reactive functional groups, as illustrated above and in the examples herein.

Advantageously, those starting materials should be used in said reactions, that lead to the formation of those compounds indicated above as being preferred.

The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers (as antipodes), or as mixtures of optical isomers such as racemates, or as mixtures of geometric isomers.

In case geometric or diastereomeric mixtures of the above compounds of intermediates are obtained, these can be separated into the single racemic or optically active isomers by methods in themselves known, e.g. by fractional distillation, crystallization and/or chromatography.

The racemic products of formula I, Ia or II, or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Any acidic intermediates can be resolved by separation of e.g. the d- and l-(alpha-methylbenzylamine, cinchonidine, cinchonine, quinine, quinidine, ephedrine, dehydroabietylamine, brucine or strychnine)-salts of any compounds having an acidic salt-forming group.

Advantageously, the more active of the antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salt can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention additionally relates to the use in mammals of the compounds of formula I, Ia or II and their pharmaceutically acceptable, non-toxic acid addition salts, or pharmaceutical compositions thereof, as medicaments, particularly as serotonin-2 blockers (antagonists of serotonin at serotonin-2 receptors), for the treatment of disorders responsive to serotonin-2 blockade, i.e. namely of psychotropic disorders such as anxiety, depression or mania, of gastrointestinal disorders such as ulcers, and of cardiovascular disorders such as hypertension.

More specifically, the invention relates advantageously to the method of treatment of psychotropic dosorders in mammals e.g. such responsive to serotonin-2 blockade, particularly anxiety, using an effective amount of a compound of the invention, e.g. of formula I, Ia, or II, or pharmaceutically acceptable salt of such compounds as pharmacologically active substances, preferably in the form of pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 5 and 100 mg of the active ingredient.

The present invention also relates to the use of the compounds of the invention for the preparation of pharmaceutical compositions, especially pharmaceutical compositions having serotonin receptor modulating activity, particularly serotonin-2 blocking activity.

The pharmaceutical compositions according to the invention are those suitable for enteral, such as oral or rectal, transdermal and parenteral administration to mammals, including man, for the treatment of diseases responsive to the antagonism of serotonin at serotonin-2 receptors, comprising an effective amount of a pharmacologically active compound of formula I, Ia or II or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethyleneglycol; for tablets also (c) binders, e.g. magnesium alumnium silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain preferably about 1 to 50% of the active ingredient.

Suitable formulations for transdermal application include an effective amount of a compound of formula I, Ia or II with carrier. Advantageous carriers include absorbable pharmaceutically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. MS, IR, NMR).

EXAMPLE 1

(a)

(±)-[4R*,4aS*,10bR*]-4-(Hydroxymethyl)-1,3,4,4a5,10b-hexahydro-9-methoxy-2H-[1]benzopyrano[4,3-c]pyridine To a stirred suspension of 8.3 g (±)-methyl [4R*,4aS*,10bR*]-1,3,4,4a,5,10b-hexahydro-9-methoxy-3-oxo-2H-[1]benzopyrano[4,3-c]pyridine-4-carboxylate in 40 ml THF under nitrogen is added 175 ml borane (1M in THF). The reaction mixture is refluxed 5 h, cooled and quenched with 5 ml $H_2O$ followed by 100 ml 6N HCl. The reaction mixture is then refluxed 30 min., cooled, concentrated under reduced pressure and basified with 120 ml 6N NaOH. The aqueous phase is extracted with six 50 ml portions of $CH_2Cl_2$ which are dried over $Na_2SO_4$, filtered and concentrated to give the title compound; m.p. 282°–283° (HCl salt).

The starting material is prepared as follows:

To stirred solution of 79 g of 6-methoxy-2H-[1]benzopyran (J. Org. Chem. 1973, 38, 3832) and 17.6 g of cuprous iodide-trimethyl phosphite (Synthesis 1971, 658) in 400 ml toluene, is added at 103° 125 g dimethyl diazomalonate (Synthesis 1971, 658) over a period of 30 min. After stirring 1.5 h, the reaction mixture is cooled, filtered through Celite, concentrated under reduced pressure and flash chromatographed with ethyl acetate/hexane (3:7) to give cis-(±)-dimethyl 1,1a,2,7b-tetrahydro-6-methoxybenzo[b]cyclopropa[d]pyran-1,1-dicarboxylate.

Under nitrogen 425 ml of diethylaluminum cyanide (1.5M in toluene) is added to 93 g cis-dimethyl 1,1a,2,7b-tetrahydro-6-methoxybenzo[b]cyclopropa[d]-pyran-1,1-dicarboxylate in 1250 ml toluene. After stirring 2 h at 25°, the reaction mixture is poured into 1250 ml 17.4% HCl. The aqueous phase is separated and extracted with three 100 ml portions of ethyl acetate and three 200 ml portions of $CH_2Cl_2$. The combined organic phases are washed with 500 ml 2N HCl, 500 ml brine, dried over $Na_2SO_4$, filtered and concentrated under reduced pressure to give trans(±)-dimethyl 2-(3,4-dihydro-6-methoxy-4-cyano-2H-[1]benzopyran-3-yl)-propanedioate.

To a solution of 96 g trans dimethyl 2-(3,4-dihydro-6-methoxy-4-cyano-2H-[1]benzopyran-3-yl)propanedioate in 1600 ml glacial acetic acid is added 10 g PtO$_2$. The reaction mixture is hydrogenated at 45 psi for 2 h. The reaction mixture is filtered through a pad of Celite and concentrated to dryness under reduced pressure. This residue is stirred with 100 ml boiling methanol and allowed to cool. The title compound is filtered off, washed with 50 ml cold methanol-ether (1:1) and dried in vacuo to afford (±)-methyl[4R*,4aS*,10bR*]-1,3,4,4a5,10b-hexahydro-9-methoxy-3-oxo-2H-[1]benzopyrano-[4,3-c]pyridine-4-carboxylate; m.p. 206°–210°.

Similarly prepared are:
(b) (±)-[4R*,4aS*,10bR*]-4-(Hydroxymethyl)-1,3,4,4a,5,10b-hexahydro-7-methoxy-2H-[1]benzopyrano[4,3-c]pyridine; m.p. 135°–145° (HCl salt);
(c) (±)-[4R*,4aS*,10bR*]-4-(Hydroxymethyl)-1,3,4,4a,5,10b-hexahydro-10-methoxy-2H-[1]benzopyrano[4,3c]pyridine; m.p. 233°–234° (HCl salt).

EXAMPLE 2

(a)

(±)-[4R*,4aS*,10bR*]-7-Bromo-4-(hydroxymethyl)-1,3,4,4a,5,10b-hexahydro-9-methoxy-2H-[1]benzopyrano[4,3-c]pyridine To a stirred solution of 8.66 g (±)-[4R*,4aS*,10bR*]-4-(hydroxymethyl)-1,3,4,4a,5,10b-hexahydro-9-methoxy-2H-[1]benzopyrano[4,3-c]pyridine in 90 ml acetic acid is added dropwise 1.96 ml bromine at 25°. After stirring 1.5 h, the solution is concentrated under reduced pressure and treated with 100 ml 2N NaOH. The aqueous phase is extracted with three 100 ml portions of CH$_2$Cl$_2$. The organic extracts are dried over Na$_2$SO$_4$, filtered, concentrated and flash chromatographed with CH$_2$Cl$_2$/ammonia saturated methanol (90:10) to give the title compound as the major product; m.p. 281°–285° dec (HCl salt).

Also obtained as minor products are:
(b) (±)-[4R*,4aS*,10bR*]-7,10-dibromo-4-(hydroxymethyl)-1,3,4,4a,5,10b-hexahydro-9-methoxy-2H-[1]benzopyrano[4,3-c]pyridine; m.p. 223°–224° (free base);
(c) (±)-[4R*,4aS*,10bR*]-8-Bromo-4-(hydroxymethyl)-1,3,4,4a,5,10b-hexahydro-9-methoxy-2H-[1]benzopyrano[4,3-c]pyridine; m.p. 268°–270° dec (HCl salt).

EXAMPLE 3

(±)-[4R*,4aS*,10bR*]-7-Bromo-4-(hydroxymethyl)-1,3,4,4a,5,10b-hexahydro-9-methoxy-2-methyl-2H-[1]benzopyrano[4,3-c]pyridine A solution of 1.65 g (±)-[4R*,4aS*,10bR*]-7-bromo-4-(hydroxymethyl)-1,3,4,4a,5,10b-hexahydro-9-methoxy-2H-[1]benzopyrano[4,3-c]pyridine in 0.5 ml 37% HCHO and 2.2 ml HCO$_2$H is heated at 100° for 20 min. The reaction mixture is concentrated in vacuo and partitioned between 10 ml 2N NaOH and 50 ml CH$_2$Cl$_2$. The organic phase is dried over Na$_2$SO$_4$, filtered and concentrated under reduced pressure to yield the title compound; m.p. of HCl salt 262° dec.

EXAMPLE 4

(±)-[4R*,4aS*,10bR*]-7-Bromo-4-(ethylthiomethyl)-1,3,4,4a,5,10b-hexahydro-9-methoxy-2-methyl-2H-[1]benzopyrano[4,3-c]pyridine To a stirred solution of 0.46 ml ethanethiol in 40 ml dry tetrahydrofuran (THF) under nitrogen at −10° is added dropwise 2.3 ml n-butyllithium (2.28M in hexane). This solution is added to a solution of 1.91 g (±)-[4R*,4aS*,10bR*]-7-bromo-4-(methylsulfonyloxymethyl)-1,3,4,4a,5,10b-hexahydro-9-methoxy-2-methyl-2H-[1]benzopyrano[4,3-c]pyridine in 25 ml THF. After stirring 2 h at 25°, 5 ml H$_2$O is added and the reaction mixture concentrated under reduced pressure. The residue is partitioned between 25 ml H$_2$O and 50 ml CH$_2$Cl$_2$. The CH$_2$Cl$_2$ phase is washed with 20 ml H$_2$O, dried over Na$_2$SO$_4$, filtered and concentrated. Flash chromatography with CH$_2$Cl$_2$/MeOH (40:1) yields an oil which is dissolved in 40 ml isopropyl alcohol. The solution is warmed at 50° and 1 ml 3.4N HCl/ethyl acetate is added. After cooling overnight the product is filtered, washed with isopropyl alcohol/ether (1:1) and dried to afford the title compound, m.p. 268°–269° dec (HCl salt).

The starting material is prepared as follows:

To a solution of 1.69 g of (±)-[4R*,4aS*,10bR*]-7-bromo-4-(hydroxymethyl)-1,3,4,4a,5,10b-hexahydro-9-methoxy-2-methyl-2 H-[1]benzopyrano[4,3-c]pyridine and 0.82 ml triethylamine in 60 ml CH$_2$Cl$_2$ is added 0.42 ml of methanesulfonyl chloride. After 15 min. 1 drop methanol is added and the reaction mixture is washed with saturated NaHCO$_3$ and dried over Na$_2$SO$_4$. Filtration and removal of solvents under reduced pressure yields (±)-[4R*,4aS*,10bR*]-7-bromo-4-(methylsulfonyloxymethyl)-1,3,4,4a,5,10b-hexahydro-9-methoxy-2-methyl-2H-[1]benzopyrano[4,3-c]pyridine.

EXAMPLE 5

(±)-[4R*,10bS*]-1,3,4,4a,5,10b-Hexahydro-2H-[1]benzopyrano[4,3-c]pyridine

To a suspension of 0.181 g of lithium aluminum hydride in 40 ml THF is added a solution of 0.590 g (±)-[4aR*,10bS*]-1,3,4,4a,5,10b-hexahydro-3-oxo-2H-[1]benzopyrano[4,3-c]pyridine in 5 ml THF. After stirring 3 h at 50°, the reaction mixture is cooled and 0.18 ml H$_2$O, followed by 0.18 ml 15% NaOH and 0.54 ml H$_2$O is added. The mixture is stirred with 2 g Na$_2$SO$_4$ filtered through Celite and evaporated to dryness under reduced pressure to afford the title compound; m.p. of HCl salt 314°–318°.

The starting material is prepared as follows:

Eleven grams 2H-[1]benzopyran-4-one are dissolved in 33 ml 2.5M trimethylsilyl cyanide (CH$_2$Cl$_2$). After addition of 50 mg ZnI$_2$, the mixture is stirred 12 h. Then 30 ml toluene, 115 ml pyridine and 21 ml POCl$_3$ are added and the mixture refluxed for 4 h. On cooling, it is poured into 1000 ml 5% HCl and extracted with four 100 ml portions of ether. The extracts dried over Na$_2$SO$_4$, filtered, concentrated under reduced pressure and vacuum distilled (bulb-to-bulb, oven temperature 150°) to yield 4-cyano-2H[1]benzopyran.

At 25° C., 7.45 g 4-cyano-2H-[1]benzopyran and 5.5 ml dimethyl malonate in 15 ml methanol are added to a solution of 1.3 g Na in 50 ml methanol. After standing 30 min, 4 ml acetic acid are added and the reaction mixture is concentrated in vacuo. The residue is partitioned between 30 ml H$_2$O and 100 ml ethyl acetate. The organic phase is dried, filtered and concentrated under reduced pressure to yield a 1:1 mixture of cis and trans-(±)-dimethyl 2-(3,4-dihydro-4-cyano-2H-[1]benzopyran-3-yl)propanedioate.

To a solution of 13.7 g of cis and trans dimethyl 2-(3,4-dihydro-4-cyano-2H-[1]benzopyran-3-yl)propanedioate in 350 ml methanol containing 30 g finely ground Co(OAc)$_2$ are added over 30 minutes 13 g NaBH$_4$. The reaction mixture is concentrated to 50 ml under reduced pressure and partitioned between 500 ml ethyl acetate and 200 ml 2N HCl. The organic phase is washed with brine, dried over Na$_2$SO$_4$, filtered and concentrated under reduced pressure. The residue is triturated with ether/ethyl acetate to afford (±)-methyl[4R*,4aS*,10bR*]-1,3,4,4a,5,10b-hexahydro-3-oxo-2H-[1]benzopyrano[4,3-c]pyridine-4-carboxylate.

To a solution of 0.195 g KCN in 25 ml H$_2$O is added 0.41 g (±)-methyl[4R*,4aS*,10bR*]-1,3,4,4a,5,10b-hexahydro-3-oxo-2H-[1]benzopyrano[4,3-c]pyridine-4-carboxylate and the mixture is refluxed 3 hours. After adding 1.6 ml 2N HCl, the solvent is removed in vacuo and the residue heated to 180° for 10 minutes. The solid is extracted with 60 ml hot ethanol. Concentration of the ethanol on the steam bath to 15 ml gives on cooling and filtering (±)-[4aR*,10bS*]-1,3,4,4a,5,10b-hexahydro-3-oxo-2H-[1]-benzopyrano[4,3-c]pyridine.

EXAMPLE 6

(±)-[4aR*,10bS*]-1,3,4,4a,5,10b-Hexahydro-2-propyl-2H-[1]benzopyrano[4,3-c]pyridine A solution of 0.235 g (±)-[4aR*,10bS*]-1,3,4,4a,5,10b-hexahydro-2H-[1]benzopyrano[4,3-c]pyridine in 5 ml toluene is refluxed with 200 mg iodopropane and 3 ml saturated NaHCO$_3$ solution for 2 hours. The organic phase is separated, dried over Na$_2$SO$_4$, filtered, concentrated in vacuo, and flash chromatographed with CH$_2$Cl$_2$/ammonia saturated methanol (95:5)to give the title compound; m.p. HCl salt 245°–247°.

EXAMPLE 7

(±)-[4aR*,10bS*]-1,3,4,4a,5,10b-Hexahydro-10-hydroxy-2-propyl-2H-[1]benzopyrano[4,3-c]pyridine To a solution of 0.48 g of diphenylphospine in 4 ml THF under nitrogen at 0° is added 1.38 ml n-butyllithium (2.24M in hexane). After 3 min., 0.238 g (±)-[4aR*,10bS*]-1,3,4,4a,5,10b-hexahydro-1-methoxy-2-propyl-2 H-[1]benzopyrano[4,3-c]pyridine in 1 ml THF is added. The mixture is refluxed 2.5 hours. After cooling 8 ml 2N HCl is added and the THF evaporated under reduced pressure. The aqueous phase is extracted with two 10 ml portions of ether, basified with solid NaHCO$_3$ and extracted with six 20 ml portions of CH$_2$Cl$_2$. The CH$_2$Cl$_2$ extracts are dried over Na$_2$SO$_4$, filtered, concentrated under reduced pressure and flash chromatographed with CH$_2$Cl$_2$/ammonia saturated methanol (20:1) to yield the title compound; m.p. of HCl salt 264°–265° dec.

EXAMPLE 8

Prepared according to procedures described in the previous examples are:

(a) (±)-[4R*,4aS*,10bR*]-7-Bromo-4-(methylthiomethyl)-1,3,4,4a,5,10b-hexahydro-9-methoxy-2-methyl-2H-[1]benzopyrano[4,3-c]pyridine hydrochloride, m.p. 279°–280° dec.

(b) (±)-[4R*,4aS*,10bR*]-7-Bromo-4-(n-propylthiomethyl)-1,3,4,4a,5,10b-hexahydro-9-methoxy-2-methyl-2H-[1]benzopyrano[4,3-c]pyridine hydrochloride, m.p. 252°–253° dec.

(c) (±)-[4R*,4aS*,10bR*]-7-Bromo-4-(n-butylthiomethyl)-1,3,4,4a,5,10b-hexahydro-9-methoxy-2-methyl-2H-[1]benzopyrano[4,3-c]pyridine hydrochloride, m.p. 235°–236°.

(d) (±)-[4R*,4aS*,10bR*]-7-Bromo-4-methoxymethyl-1,3,4,4a,5,10b-hexahydro-9-methoxy-2-methyl-2H-[1]benzopyrano[4,3-c]pyridine hydrochloride, m.p. 281–282 dec., using potassium methoxide instead of ethanethiol/butyllithium in last step of procedure of example 4.

(e) (±)-[4R*,4aS*,10bR*]-7-Bromo-4-cyanomethyl-1,3,4,4a,5,10b-hexahydro-9-methoxy-2-methyl-2H-[1]benzopyrano[4,3-c]pyridine hydrochloride, m.p. 315° dec., using potassium cyanide instead of ethanethiol/butyllithium in last step of procedure in example 4.

(f) (±)-[4R*,4aS*,10bR*]-7-Bromo-4-(phthalimidomethyl)-1,3,4,4a,5,10b-hexahydro-9-methoxy-2-methyl-2H-[1]benzopyrano[4,3-c]pyridine hydrochloride, m.p. 273°–275° dec., using potassium phthalimide instead of ethanethiol/butyllithium in last step of procedure of example 4.

(g) (±)-[4R*,4aS*,10bR*]-4-(Methylthiomethyl)-1,3,4,4a,5,10b-hexahydro-2-propyl-2H-[1]benzopyrano[4,3-c]pyridine hydrochloride, m.p. 220°–222°.

(h) (±)-[4aR*,10bS*]-1,3,4,4a,5,10b-Hexahydro-10-methoxy-2-propyl-2H-[1]benzopyrano[4,3-c]pyridine hydrochloride, m.p. 252° dec.

(i) (±)-[4aR*,10bS*]-7-Bromo-1,3,4,4a,5,10b-hexahydro-9-methoxy-2-methyl-2H-[1]benzopyrano[4,3-c]pyridine hydrochloride, m.p. 307° dec.

EXAMPLE 9

(±)-[4aR*,10bS*]-7-Bromo-1,3,4,4a,5,10b-hexahydro-9-hydroxy-2-methyl-2H-[1]benzopyrano[4,3-c]pyridine A mixture of 0.5 g (±)[4aR*,10bS*]-7-bromo-1,3,4,4a,5,10b-hexahydro-9-methoxy-2-methyl-2H-[1]benzopyrano[4,3-c]pyridine and 5 g pyridine hydrochloride is heated under nitrogen at 200° for 20 minutes. The cooled reaction mixture is dissolved in water and basified with 6N NaOH. The aqueous phase is extracted with three 25 ml portions of CH$_2$Cl$_2$, the extracts are dried over Na$_2$SO$_4$, filtered, concentrated under reduced pressure, and flash chromatographed with methylene chloride/ammonia saturated methanol (10:1) to afford the title compound; m.p. HCl salt 259°–262°.

EXAMPLE 10

(a)

(±)-[4aR*,4aS*,10bS*]-7-Bromo-1,3,4,4a,5,10b-hexahydro-9-benzyloxy-2-methyl-2H-[1]benzopyrano[4,3-c]pyridine To a solution of 0.380 g (±)-[4aR*,10bS*]-7-bromo-1,3,4,4a,5,10b-hexahydro-9-hydroxy-2-methyl-2H-[1]benzopyrano[4,3-c]pyridine in 6 ml chlorobenzene are added 0.191 ml benzyl chloride, 0.290 g benzyltriethylammonium chloride and 2 ml 50% NaOH. The reaction mixture is stirred vigorously for 2 hours. The organic phase is separated, dried over Na$_2$SO$_r$, filtered and concentrated under reduced pressure. Flash chromatography with CH$_2$Cl$_2$/ammonia saturated methanol (20:1) gives the title compound; m.p. of HCl salt 283° dec.

Similarly prepared are:
(b) (±)-[4aR*,10bS*]-1,3,4,4a,5,10b-Hexahydro-9-(1-naphthylmethoxy)-2-methyl-2H[1]-benzopyrano[4,3-c]pyridine hydrochloride, m.p. 196 dec.
(c) (±)-[4aR*,10bS*]-1,3,4,4a,5,10-Hexahydro-9-(1-fluorenylmethoxy)-2-ethyl-2H[1]-benzopyrano[4,3-c]pyridine fumarate, m.p. 202°–204°.
(d) (±)-[4aR*,10bS*]-1,3,4,4a,5,10b-Hexahydro-9-(9-fluorenyloxy)2-ethyl-2H[1]-benzopyrano[4,3-c]pyridine fumarate, m.p. 200°–202° dec.
(e) bis-[(±)-[4aR*,10bS*]-1,3,4,4a,5,10b-Hexahydro-2,7-dimethyl-2H[1]-benzopyrano[4,3-c]pyridin-9-yloxy]methane dihydrochloride, m.p. 281°–221° dec., using diiodomethane as reagent.
(f) bis-[(±)-[4aR*,10bS*]-1,3,4,4a,5,10b-Hexahydro-2H[1]-benzopyrano[4,3-c]pyridin-9-yloxy]-methane dihydrochloride, m.p. 258° dec., using diiodomethane.
(g) bis-[(±)-[4aR*,10bS*]-1,3,4,4a,5,10b-Hexahydro-7-bromo-2-methyl-2H[1]-benzopyrano[4,3-c]pyridin-9-yloxy]-methane dihydrochloride, m.p. 274°–276°, using diiodomethane as reagent.
(h) (±)-[4aR*,10bS*]-1,3,4,4a,5,10b-Hexahydro-7-bromo-2-methyl-9-isopropyloxy-2H[1]-benzopyrano[4,3-c]pyridine hydrochloride, m.p. 210°–215° dec.

EXAMPLE 11

(a)

(±)-[4aR*,10bS*]-1,3,4,4a,5,10b-Hexahydro-9-(phenylethyloxy)-2-methyl-2H-[1]benzopyrano[4,3-c]pyridine A mixture of 0.2 g (±)-[4aR*,10bS*]-1,3,4,4a,5,10b-hexahydro-9-hydroxy-2-methyl-2H-[1]benzopyrano[4,3-c]pyridine (m.p. of HCl salt 268°–269°), 0.215 ml phenethyl alcohol and 0.3 g dicyclohexylcarbodiimide is heated under nitrogen for 18 hours at 130°. The cooled reaction mixture is flash chromatographed with $CH_2Cl_2$/methanol (20:1) to yield the title compound; m.p. HCl salt 204°.

Similarly prepared are:
(b) (±)-[4aR*,10bS*]-1,3,4,4a,5,10b-Hexahydro-9-(1-naphthylethyloxy)-2H[1]-benzopyrano[4,3-c]pyridine hydrochloride, m.p. 120°–125° dec.
(c) (±)-[4aR*,10bS*]-1,3,4,4a,5,10b-Hexahydro-9-(2-naphthylethyloxy)-2-methyl-2H[1]-benzopyrano[4,3-c]pyridine hydrochloride, m.p. 136°–140°.

EXAMPLE 12

(±)-[4aR*,10bS*]-1,3,4,4a,5,10b-Hexahydro-9-methoxy-2,7-dimethyl-2H-[1]benzopyrano[4,3-c]pyridine To a solution of 1.2 g (±)-[4aR*,10bS*]-7-bromo-1,3,4,4a,5,10b-hexahydro-9-methoxy-2-methyl-2H-[1]benzopyrano[4,3-c]pyridine in 25 ml dry THF is added 2.14 ml n-butyllithium (1.98M in hexane). After 30 minutes 0.36 ml $CH_3I$ is added and the reaction is warmed to 25° and stirred 1 hour. Water (50 ml) and ethyl acetate (100 ml) is added. The organic phase is washed with brine, dried over $Na_2SO_4$, filtered, concentrated under reduced pressure, and flash chromatrographed with $CH_2Cl_2$/ammonia saturated methanol (20:1) to afford the title compound; m.p. HCl salt 263° dec.

EXAMPLE 13

(±)-[4R*,4aS*,10bR*]-4-(Aminomethyl)-7-bromo-1,3,4,4a,5,10b-hexahydro-9-methoxy-2-methyl-2H[1]-benzopyrano[4,3-c]pyridine To suspension of 0.305 g (±)-[4R*,4aS*,10bR*]-7-bromo-1,3,4,4a,5,10b-hexahydro-9-methoxy-2-methyl-4-(phthalimidomethyl)-2H-[1]benzopyrano[4,3-c]pyridine in 40 ml MeOH, is added 0.102 ml hydrazine hydrate. The mixture is refluxed 12 hours, cooled, acidified to pH 1 with 12N HCl, and concentrated to a 3 ml volume under reduced pressure. The residue is partitioned between 10 ml 2N NaOH and $CH_2Cl_2$ (40 ml). The organic phase is dried over $MgSO_4$, filtered, and evaporated to dryness in vacuo to yield the title compound; m.p. HCl salt 277°–279° dec.

EXAMPLE 14

(±)-[4R*,4aS*,10bR*]-4-(Benzyloxycarbonylaminomethyl)-7-bromo-1,3,4,4a,5,10b-hexahydro-9-methoxy-2-methyl-2H[1]-benzopyrano[4,3-c]pyridine To a stirred mixture of 0.130 g (±)-[4R*,4aS*,10bR*]-7-bromo-4-(aminomethyl)-1,3,4,4a,5,10b-hexahydro-9-methoxy-2-methyl-2H-[1]benzopyyrano[4,3-c]pyridine in 2 ml toluene and 0.106 g $Na_2CO_3$ in 0.4 ml $H_2O$ is added 0.06 ml benzyl chlorofomate. After stirring 5 min., the organic phase is separated, dried over $Na_2SO_4$, filtered, and evaporated to dryness in vacuo to yield title compound; m.p. HCl salt 159°–161°.

EXAMPLE 15

Prepared according to procedures described in the previous examples are:
(a) (±)-[4aR*,10bS*]-1,3,4,4a,5,10b-Hexahydro-2-methyl-2H[1]-benzopyrano[4,3-c]pyridine hydrochloride, m.p. 293°–300°.
(b) (±)-[4abS*]-1,3,4,4a,5,10b-Hexahydro-8-bromo-2-methyl-2H[1]-benzopyrano[4,3-c]pyridine hydrochloride, m.p. 282°–286°.
(c) (±)-[4aR*,10bS*]-1,3,4,4a,5,10b-Hexahydro-7-methoxy-2H[1]-benzopyrano[4,3-c]pyridine hydrochloride, m.p. 284°–285°.
(d) (±)-[4aR*,10bS*]-1,3,4,4a,S,10b-Hexahydro-7-bromo-10-methoxy-2H[1]benzopyrano[4,3-c]pyridine hydrochloride, m.p. 272°–274° dec.
(e) (±)-[4aR*,10bS*]-1,3,4,4a,5,10b-Hexahydro-7-bromo-10-methoxy-2-methyl-2H[1]benzopyrano[4,3-c]pyridine hydrochloride, m.p. 249°–251°.
(f) (±)-[4aR*,10bS*]-1,3,4,4a,5,10b-Hexahydro-10-methoxy-2-methyl-2H[1]benzopyrano[4,3-c]pyridine hydrochloride, m.p. 221°–222°.
(g) (±)-[4aR*,10bS*]-1,3,4,4a,5,10b-Hexahydro-10-methoxy-2,7-dimethyl-2H[1]-benzopyrano[4,3-c]pyridine hydrochloride, m.p. 212°–214°.
(h) (±)-[4aR*,10bS*]-1,3,4,4a,5,10b-Hexahydro-9-bromo-10-methoxy-2,7-dimethyl-2H[1]-benzopyrano[4,3-c]pyridine hydrochloride, m.p. 182°–183° dec.
(i) (±)-[4aR*,10bS*]-1,3,4,4a,5,10b-Hexahydro-7-bromo-10-methoxy-2-propyl-2H[1]-benzopyrano[4,3-c]pyridine hydrochloride, m.p. 247°–248° dec.
(j) (±)-[4aR*,10bS*]-1,3,4,4a,5,10b-Hexahydro-10-methoxy-2,7-dipropyl-2H[1]-benzopyrano[4,3-c]pyridine hydrochloride, m.p. 140°–141° dec.

(k) (±)-[4aR*,10bS*]-1,3,4,4a,5,10b-Hexahydro-10-methoxy-7-methyl-2-propyl-2H[1]-benzopyrano[4,3-c]pyridine hydrochloride, m.p. 220°-221° dec.

(l) (±)-[4aR*,10bS*]-1,3,4,4a,5,10b-Hexahydro-7-bromo-9-methoxy-2H[1]-benzopyrano[4,3-c]pyridine hydrochloride, m.p. 302°-303° dec.

(m) (±)-[4aR*,10b*]-1,3,4,4a,5,10b-Hexahydro-9-methoxy-2-methyl-2H[1]benzopyrano[4,3-c]pyridine hydrochloride, m.p. 269°-270° dec.

(n) (±)-[4aR*,10bS*]-1,3,4,4a,5,10b-Hexahydro-8-bromo-9-methoxy-2-methyl-2H[1]benzopyrano[4,3-c]pyridine hydrochloride, m.p. 282°-283° dec.

(o) (±)-[4aR*,10bS*]-1,3,4,4a,5,10b-Hexahydro-8-bromo-9-hydroxy-2H[1]benzopyrano[4,3-c]pyridine hydrochloride, m.p. 302° dec.

(p) (±)-[4aR*,10bS*]-1,3,4,4a,5,10b-Hexahydro-8-bromo-9-methoxy-2H[1]benzopyrano[4,3-c]pyridine hydrochloride, m.p. 314° dec.

(q) (±)-[4aR*,10bS*]-1,3,4,4a,5,10b-Hexahydro-7-bromo-9-methoxy-2-propyl-2H[1]benzopyrano[4,3-c]pyridine hydrochloride, m.p. 288° dec.

(r) (±)-[4aR*,10bS*]-1,3,4,4a,5,10b-Hexahydro-7,9-dimethoxy-2H[1]benzopyrano[4,3-c]pyridine hydrochloride, m.p. 231°-233°.

(s) (±)-[4aR*,10bS*]-1,3,4,4a,5,10b-Hexahydro-7-bromo-9-methoxy-2-[3-(p-fluorobenzoyl)-propyl]-2H[1]benzopyrano[4,3-c]pyridine hydrochloride, m.p. 245°-250° dec.

(t) (±)-[4aR*,10bS*]-1,3,4,4a,5,10b-Hexahydro-7-bromo-2-ethyl-9-methoxy-2H[1]benzopyrano[4,3-c]pyridine hydrochloride, m.p. 293° dec.

(u) (±)-[4aR*,10bS*]-1,3,4,4a,5,10b-Hexahydro-7-ethyl-9-methoxy-2-methyl-2H[1]benzopyrano[4,3-c]pyridine hydrochloride, m.p. 236°-239°

(v) (±)-[4aR*,10bS*]-1,3,4,4a,5,10b-Hexahydro-9-methoxy-7-propyl-2-methyl-2H[1]benzopyrano[4,3-c]pyridine hydrochloride, m.p. 188°-190°.

(w) (±)-[4aR*,10bS*]-1,3,4,4a,5,10b-Hexahydro-7-bromo-9-methoxy-2-allyl-2H[1]benzopyrano[4,3-c]pyridine hydrochloride, m.p. 273°-274° dec.

(x) (±)-[4R*,4aS*,10bR*]-1,3,4,4a,5,10b-Hexahydro-4-ethylthiomethyl-9-methoxy-2-methyl-2H[1]benzopyrano[4,3-c]pyridine hydrochloride, m.p. 192°-194°.

EXAMPLE 16

Prepared according to procedures described in the previous examples for the compounds of formula I wherein X represents oxygen are the following compounds of formula I wherein X represents sulfur, starting from the appropriately substituted 2H-[1]benzothiopyran-4-ones (thiochroman-4-ones):

(a) (±)-[4aR*,10bS*]-1,3,4,4a,5,10b-Hexahydro-2-methyl-2H-[1]benzothiopyrano[4,3-c]pyridine hydrochloride, m.p. 237°-251° dec.

(b) (±)-[4aR*,10bS*]-1,3,4,4a,5,10b-Hexahydro-7-methyl-9-methoxy-2H-[1]benzothiopyrano[4,3-c]pyridine hydrochloride, m.p. 245°-247°.

(c) (±)-[4aR*,10bS*]-1,3,4,4a,5,10b-Hexahydro-2,7-dimethoxy-9-methoxy-2-H[1]benzothiopyrano[4,3-c]pyridine hydrochloride, m.p. 243°-245°.

(d) (±)-[4R*,4aS*,10bR*]-7-Bromo-4-(ethylthiomethyl)-1,3,4a,5,10b-hexahydro-9-methoxy-2-methyl-2H[1]benzothiopyrano[4,3-c]pyridine.

The starting 2H-[1]-benzothiopyran-4-ones are prepared as exemplified below:

To 71 g Cl$_2$ in 1000 ml acetic acid is added at 0° 98 g KSCN. After 30 minutes 75 g m-bromoanisole is added and the mixture stirred 12 hours. It is then poured in 4000 ml H$_2$O and extracted with two 1000 ml portions of hexane/ether (1:1). The combined extracts are washed with 1000 ml saturated NaHCO$_3$, 500 ml brine, dried over Na$_2$SO$_4$, filtered, concentrated under reduced pressure and distilled to yield 2-bromo-4-methoxy-benzenethiocyanate, bp (0.1 mm) 140°-145°.

To a solution of 10.8 g Na in 1200 ml anhydrous ethanol are added under nitrogen 21 g of above thiocyanate in 25 ml ethanol. The reaction is stirred 1 hour and quenched with 29 ml acetic acid. Six hundred ml H$_2$O are added and the mixture is extracted with four 150 ml portions of hexane/ether (1:1). The combined extracts are washed with 500 ml H$_2$O, dried over Na$_2$SO$_4$, filtered and concentrated under reduced pressure to give 4-methoxy-2-methylbenzenethiol.

A mixture of 16.1 g 4-methoxy-2-methylbenzenethiol, 20 g 3-chloropropionic acid and 31.5 g CsF in 200 ml CH$_3$CN is refluxed 40 hours. The cooled reaction mixture is poured into 200 ml 1N NaOH, and washed with 500 ml ether. The aqueous phase is acidified with 12N HCl and extracted with three 100 ml portions of CH$_2$Cl$_2$. The combined extracts are washed to 100 ml brine, dried over Na$_2$SO$_4$, filtered and evaporated to dryness in vacuo to afford 3-[(2-methyl-4-methoxyphenyl)thio]propanoic acid.

A solution of 21.1 g 3-[(2-methyl-4-methoxyphenyl)-thio]propanoic acid and 160 g polyphosphoric ester in 150 ml CHCl$_3$ is refluxed for 45 min. To the cooled reaction mixture is added 200 ml 0.5 N NaOH. The organic phase is separated and the aqueous phase is extracted with 100 ml CHCl$_3$. The combined organic extracts are dried over Na$_2$SO$_4$, filtered, concentrated under reduced pressure and flash chromatographed with ethyl acetate/hexane (8:92) to yield 6-methoxy-8-methyl-2H-[1]benzothiopyran-4-one.

EXAMPLE 17

Preparation of 10,000 tablets each containing 10 mg of the active ingredient of Example 4:
Formula:

| | |
|---|---|
| [4R*,4aS*,10bR*]-7-Bromo-4-(ethylthiomethyl)-1,3,4,4a,5,10 b-hexahydro-9-methoxy-2-methyl-2H—[1]benzopyrano[4,3-c] pyridine hydrochloride | 100.00 g |
| Lactose | 2,535.00 g |
| Corn starch | 125.00 g |
| Polyethylene glycol 6,000 | 150.00 g |
| Magnesium stearate | 40.00 g |
| Purified water | q.s |

Procedure:

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

Analogously tablets are prepared, containing 10-200 mg of one of the other compounds disclosed and exemplified herein.

EXAMPLE 18

Preparation of 1,000 capsules each containing 10 mg of the active ingredient of Example 4:
Formula:

| | |
|---|---:|
| [4R*,4aS*,10bR*]-7-Bromo-4-(ethylthiomethyl)-1,3,4,4a,5,10 b-hexahydro-9-methoxy-2-methyl-2H—[1]benzopyrano[4,3-c] pyridine hydrochloride | 10.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing 10–200 mg of the other compounds disclosed and exemplified herein.

What is claimed is:

1. A compound of the formula

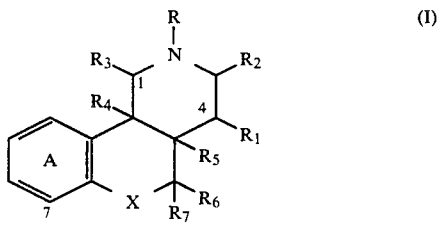

with a trans-4a,10b ring junction
  wherein X represents oxygen (O) or sulfur (S); ring A is unsubstituted or substituted by one substituent or by two or three identical or different substituents selected from hydroxy, etherified hydroxy, acyloxy, halogen, lower alkyl, aryl-lower alkyl and trifluoromethyl; or ring A is substituted on adjacent carbon atoms by one lower alkylenedioxy; R represents hydrogen, lower alkyl, lower alkenyl, lower alkynyl, aroyl-lower alkyl or aryl-lower alkyl; $R_1$ represents hydrogen, lower alkyl, lower alkylthio-lower alkyl, aryl-lower alkylthio-lower alkyl, (amino, mono- or di-lower alkylamino)-lower alkyl, acylamino-lower alkyl, (hydroxy, acyloxy or etherified hydroxy)-lower alkyl, or cyano-lower alkyl; $R_2$–$R_7$ represent hydrogen; or a pharmaceutically acceptable salt thereof; and wherein in the definitions etherified hydroxy represents lower alkoxy, lower alkenyloxy, lower alkynyloxy, $C_{3-6}$-cycloalkyl-lower alkoxy, aryl-lower alkoxy, pyridyl-($C_1$–$C_4$)-alkoxy, naphthyl-lower alkoxy, fluorenyloxy, or fluorenyl-lower alkoxy; acyloxy represents lower alkanoyloxy, aroyloxy, or heteroaroyloxy; acylamino represents lower alkanoylamino, aryl-lower alkanoylamino, aroylamino, heteroaroylamino, lower alkoxycarbonylamino or benzyloxycarbonylamino; and in said definitions aryl represents phenyl, 1- or 2-naphthyl, or phenyl substituted by one to three of lower alkyl, lower alkoxy, halogen or trifluoromethyl; aroyl represents benzoyl or benzoyl substituted by one to three of lower alkyl, lower alkoxy, halogen or trifluoromethyl; and heteroaroyl represents thienoyl, pyrroloyl, or 2-, 3- or 4-pyridylcarbonyl.

2. A compound according to claim 1 wherein X represents oxygen or sulfur; ring A is unsubstituted or substituted by one substituent or by two or three different or identical substituents selected from hydroxy, acyloxy, etherified hydroxy, aryl-lower alkyl, lower alkyl and halogen; or ring A is substituted on adjacent carbon atoms by lower alkylenedioxy; R represents hydrogen or lower alkyl; $R_1$ represents hydrogen, lower alkyl, lower alkylthio-lower alkyl or lower alkoxy-lower alkyl; $R_2$–$R_7$ represent hydrogen; or a pharmaceutically acceptable salt thereof.

3. A compound according to claim 2 wherein ring A is unsubstituted or substituted by one substituent or by two identical or different substituents selected from lower alkyl, aryl-lower alkyl, lower alkoxy, aryl-lower alkoxy and halogen; X represents oxygen or sulfur; R represents hydrogen or lower alkyl; $R_1$ represents hydrogen, lower alkyl, lower alkylthiomethyl, or lower alkoxymethyl; $R_2$–$R_7$ represent hydrogen; or a pharmaceutically acceptable salt thereof.

4. A compound according to claim 2 wherein X represents oxygen or sulfur; ring A is monosubstituted or disubstituted by identical or different substituent selected from lower alkoxy of 1 to 4 carbon atoms, benzyloxy, lower alkyl of 1 to 4 carbon atoms and halogen; R represents lower alkyl of 1 to 4 carbon atoms; $R_1$ represents hydrogen, lower alkyl of 1 to 4 carbon atoms, lower $C_1$–$C_4$-alkylthio-methyl or lower $C_1$–$C_4$-alkoxymethyl; $R_2$–$R_7$ represent hydrogen; or a pharmaceutically acceptable salt thereof.

5. A compound according to claim 2 wherein X represents oxygen.

6. A compound according to claim 2 wherein X represents sulfur.

7. A compound according to claim 2 of the formula $$\text{(II)}$$

with a trans-4a,10b ring junction wherein ring A is disubstituted, preferably at the 9 or 10 position by lower alkoxy of 1 to 4 carbon atoms, and, preferably at the 7-position by lower alkyl of 1 to 4 carbon atoms or halogen; R′ represents lower alkyl of 1 to 4 carbon atoms; $R_1'$ represents hydrogen or lower $C_1$–$C_4$-alkylthiomethyl; or a pharmaceutically acceptable salt thereof.

8. A compound according to claim 7 of formula II with a trans-4a,10b-ring junction wherein ring A is substituted at the 7-position by lower alkyl of 1 to 3 carbon atoms, bromo or chloro, and substituted at the 9-position by lower alkoxy of 1 to 3 carbon atoms; R′ represents lower alkyl of 1 to 3 carbon atoms; $R_1'$ represents hydrogen or $C_1$–$C_3$-alkylthiomethyl; or a pharmaceutically acceptable salt thereof.

9. A compound of the formula

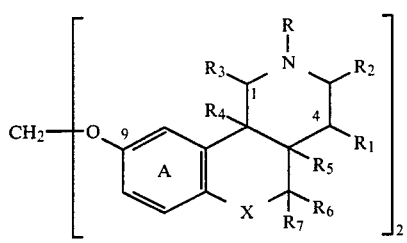

(Ia)

wherein ring A may be further substituted by a halogen, lower alkyl or trifluoromethyl group; X represents oxygen or sulfur; R represents hydrogen or lower alkyl; $R_1$ represents hydrogen, lower alkyl, lower alkylthio-lower alkyl or lower alkoxy-lower alkyl; $R_2$–$R_7$ represent hydrogen; or a pharmaceutically acceptable salt thereof.

10. A compound according to claim 7 being [4R*,4aS*,10bR*]-7-bromo-4-(ethylthiomethyl)-1,3,4,4a,5,10b-hexahydro-9-methoxy-2-methyl-2H[1]benzopyrano [4,3-c]pyridine or a pharmaceutically acceptable acid addition salt thereof.

11. A compound according to claim 7 being [4aR*,10bS*]-1,3,4,4a,5,10b-hexahydro-9-methoxy-2,7-dimethyl-2H[1]benzopyrano[4,3-c]pyridine or a pharmaceutically acceptable acid addition salt thereof.

12. A pharmaceutical composition suitable for administration to mammals for the treatment of disorders responsive to serotonin-2-blockade comprising an effective serotonin-2-blocking amount of a compound of claim 1 in combination with one or more pharmaceutically acceptable carriers.

13. A method of blocking serotonin at serotonin-2 receptors in a mammal comprising the administration to a mammal in need thereof of an effective serotonin-2 blocking amount of a compound of claim 1 or of a pharmaceutical composition comprising a compound of claim 1 in combination with one or more pharmaceutically acceptable carriers.

14. A method of treating central nervous system, cardiovascular or gastrointestinal disorders in mammals comprising the administration to a mammal in need thereof of an effective serotonin-2 blocking amount of a compound of claim 1 or of a pharmaceutical composition comprising a compound of claim 1 in combination with one or more pharmaceutically acceptable carriers.

15. A compound of the formula

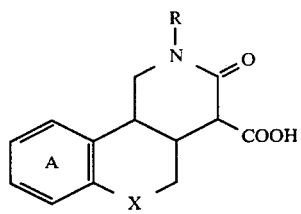

wherein X represents oxygen (O) or sulfur (S); ring A is unsubstituted or substituted by one substituent or by two or three identical or different substituents selected from hydroxy, etherified hydroxy, acyloxy, halogen, lower alkyl and trifluoromethyl; or ring A is substituted on adjacent carbon atoms by one lower alkylenedioxy; R represents hydrogen, lower alkyl, lower alkenyl, lower alkynyl, aroyl-lower alkyl or aryl-lower alkyl; or an ester derivative thereof; and wherein in the definitions etherified hydroxy represents lower alkoxy, lower alkenyloxy, lower alkynyloxy, $C_{3-6}$-cycloalkyl-lower alkoxy, aryl-lower alkoxy, pyridyl-($C_1$-$C_4$)-alkoxy, naphthyl-lower alkoxy, fluorenyloxy, or fluorenyl-lower alkoxy; acyloxy represents lower alkanoyloxy, aroyloxy, or heteroaroyloxy; and in said defintions aryl represents phenyl, 1- or 2-naphthyl, or phenyl substituted by one to three of lower alkyl, lower alkoxy, halogen or trifluoromethyl; aroyl represents benzoyl or benzoyl substituted by one to three of lower alkyl, lower alkoxy, halogen or trifluoromethyl; and heteroaroyl represents thienoyl, pyrroloyl, or 2-, 3- or 4-pyridyl-carbonyl.

* * * * *